(12) United States Patent
Blake, III

(10) Patent No.: US 8,187,287 B1
(45) Date of Patent: May 29, 2012

(54) ANTI-BACKUP MECHANISM

(76) Inventor: Joseph W Blake, III, New Canaan, CT (US)

( * ) Notice: Subject to any disclaimer, the term of this patent is extended or adjusted under 35 U.S.C. 154(b) by 1134 days.

(21) Appl. No.: 11/985,139

(22) Filed: Nov. 14, 2007

Related U.S. Application Data

(63) Continuation-in-part of application No. 11/224,487, filed on Sep. 12, 2005.

(51) Int. Cl.
*A61B 17/10* (2006.01)

(52) U.S. Cl. ........................................... 606/143

(58) Field of Classification Search .................. 606/108, 606/139–143, 171, 213, 289; 623/23.72; 227/175.1–182.1
See application file for complete search history.

(56) References Cited

U.S. PATENT DOCUMENTS 5,271,527 A * 12/1993 Haber et al. .................... 222/43
2003/0135224 A1* 7/2003 Blake, III ...................... 606/143
* cited by examiner

*Primary Examiner* — Melanie Tyson
(74) *Attorney, Agent, or Firm* — Patrick J. Walsh

(57) ABSTRACT

An anti-backup mechanism for constraining operating components in an operating mechanism to complete first and second strokes of reciprocal linear motion.

6 Claims, 6 Drawing Sheets

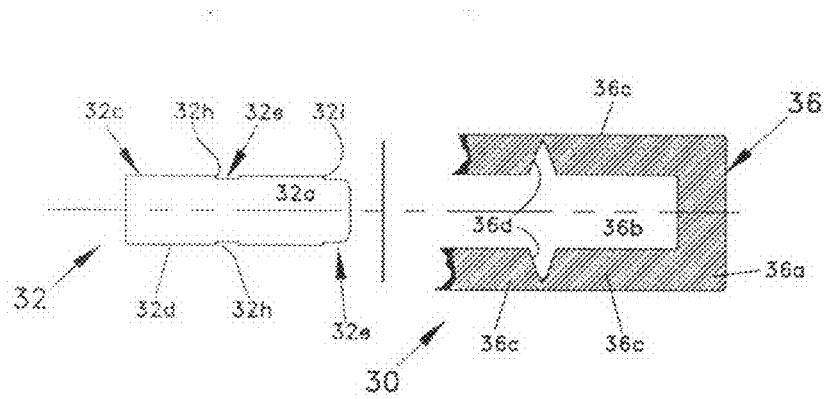
Fig. 7
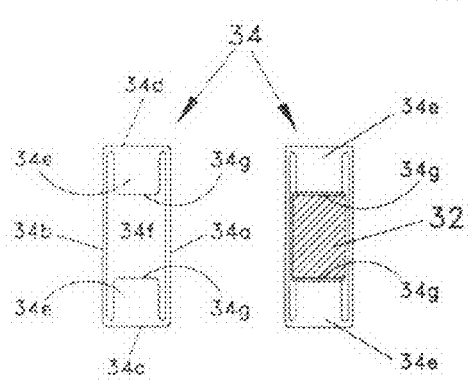
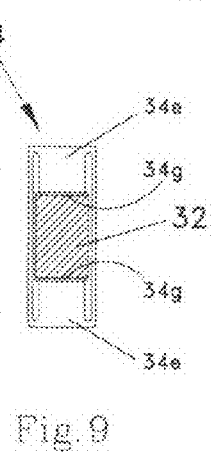
Fig. 8   Fig. 9
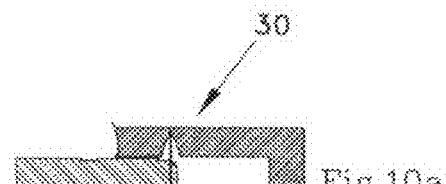
Fig. 10a
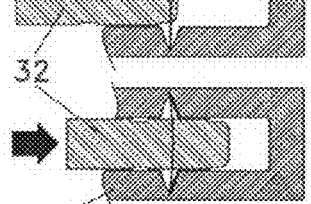
Fig. 10b
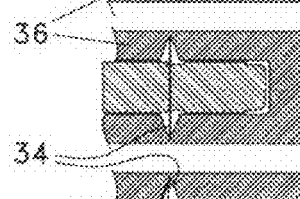
Fig. 10c
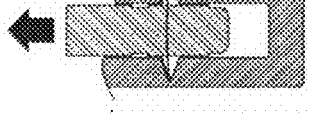
Fig. 10d
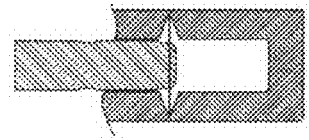
Fig. 10e

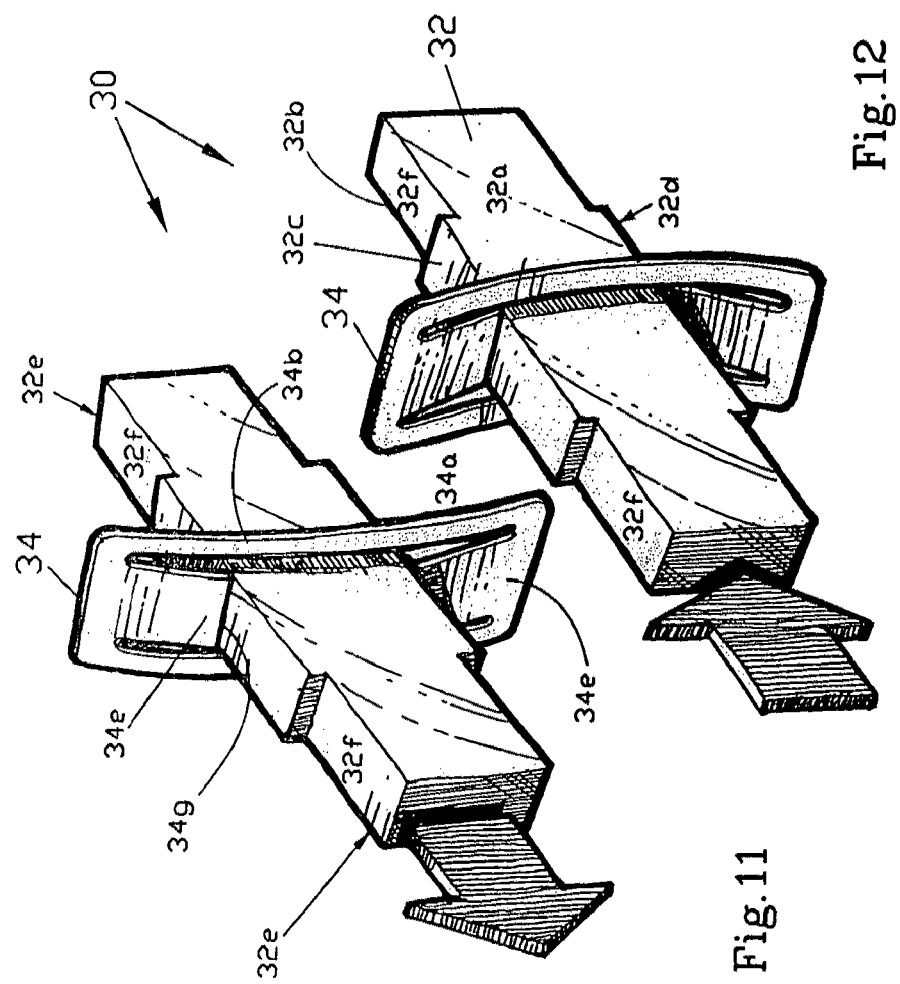

ANTI-BACKUP MECHANISM

PRIOR APPLICATION

This application is a continuation-in-part of U.S. patent application Ser. No. 11/224,487 filed Sep. 12, 2005.

BACKGROUND OF THE INVENTION

The present invention relates to surgical clip appliers embodied as an instrument having a supply of clips for rapidly deploying several clips in closing severed blood vessels and other small fluid carrying ducts in surgical procedures. There are many different designs for surgical clip applicators for a variety of surgical procedures including both open surgery and laparoscopy in which a clipping appliance fits through a trocar tube into a body cavity where the clips are applied.

A surgical clip applicator comprises an operating handle and clip applying mechanism having an operating cycle in which operating levers are squeezed together and released. In this operating cycle, a clip is applied in surgery and the clip applicator jaws are reloaded with a single clip from a clip supply channel for clip application in the next cycle. The applicator provides a moveable clip supply channel containing a line of clips that are released seriatim. The supply channel integrates a clip pusher and an escapement or clip stop spring in a single unit.

A well-known hazard with clip appliers is a condition of releasing a partially closed clip in a surgical site. This condition results when operating handles are given a partial pull or closing and then released. The partial pull crimps but does not close a clip located in the instrument jaws. When partially pulled handles of some older instruments are released, the instrument jaws re-open and the partially closed clip falls from the jaws into the surgical site.

This invention provides an anti-backup mechanism for a repeating multi-clip applier to prevent this operating hazard.

The present invention also relates generally to mechanical devices used in applications other than clip appliers, where such devices have reciprocal motion in one or more components, and where it is desirable for proper operation of the devices to ensure that full reciprocal motion of components occurs in operating or using the devices. The invention ensures that reciprocal translators (i.e., that component of the device which undergoes reciprocal motion) forming part of a mechanical device move through the full reciprocal excursion assigned to the translator as a component of a mechanical device. Specifically, the invention prevents reversal of movement of a reciprocal translator at a point intermediate the full excursion assigned to the translator. If a translator comes to rest at a point intermediate full excursion, the anti-backup device of the invention ensures that the translator is restricted to resuming movement only in the same direction as before it came to rest.

SUMMARY OF THE INVENTION

A preferred embodiment of repeating multi-clip applier according to the present invention comprises an instrument having an operating handle housing and a removable, fully rotatable and disposable clip applying cartridge. A full squeeze and release of operating handles applies a clip to a surgical site and reloads another clip into clip applying jaws of the instrument.

The operating handle housing accommodates an anti-backup mechanism to prevent a partial pull and release of the operating handles to prevent the hazard of a partially closed clip falling into the surgical site. The present invention prevents occurrence of this condition by means of an anti-backup mechanism to ensure that when the appliance handles are pulled, the handles must be given a full pull to execute a complete cycle of the clip applier mechanism. If a partial pull of the appliance handles occurs, the anti-backup mechanism retains or holds the clip applier mechanism in fixed position without possibility of backup or reverse. The anti-backup "hold" is released simply by giving the handles a complete pull. When a partial pull occurs and the anti-backup mechanism holds the clip applying mechanism in place, the instrument jaws remain partially closed holding a partially closed clip thereby preventing the clip from falling into a surgical site. The anti-backup mechanism also functions in the opposite, or release, motion of operating handles. That is, the operating handles when being released are constrained by the anti-backup mechanism to undergo a full release motion. The anti-backup mechanism prevents partial release and re-pull of the trigger thereby to prevent double loading of a clip into the crimping jaws, a condition that would jam the instrument.

Another embodiment of anti-backup mechanism has general application in devices having one or more components undergoing reciprocal motion during operation of the device, where it is desirable to ensure full reciprocal excursion occur in each operating use of the device. For this purpose, an anti-backup spring is held stationary along spaced edges within the device housing, with the spring itself having spring blades positioned in confronting relation across an opening in the spring. A reciprocal translator, passes through the spring opening in sliding engagement with operative edges of the spring blades. In this sliding engagement the spring blades deflect slightly in that direction of motion of the translator. An attempt to reverse motion of the translator to travel in the opposite direction is blocked by the spring blades which cooperate by engaging translator surfaces to prevent reverse motion. So, the only motion available to the translator is full excursion in the original direction to a point where the spring blades disengage the translator. Motion may be reversed only after such disengagement of the spring blades. In like manner, the spring blades engage the translator on the return excursion preventing backup motion until full return excursion occurs.

Full excursion of the translator is selected according to the task it performs as part of an operating mechanism and the translator is confined to that full excursion by locating transition points a specified distance apart on the translator body. At each transition point, the spring blades disengage the translator and motion can be reversed.

Specific examples are included in the following description for purposes of clarity, but various details can be changed within the scope of the present invention.

OBJECTS OF THE INVENTION

An object of the invention is to provide a clip applicator having an operating handle that provides anti-backup linear reciprocating motion of a clip applying cartridge.

Another object of the invention is to provide a clip applicator having an operating handle with an anti-backup mechanism that permits full forward and reverse strokes of a clip applying cartridge to avoid the hazard of releasing a partially crimped clip at a surgical site.

Another object of the invention is to provide a clip applicator having an operating handle with an anti-backup mechanism that permits full forward and reverse strokes of a clip applying cartridge to prevent double loading of a clip into the crimping jaws, a condition that would jam the instrument.

Another object of the invention is to provide an anti-backup mechanism having general application in devices with components undergoing reciprocal motion where it is desirable or necessary for the component always to complete full motion in one direction before reversal of motion is possible.

Other and further objects of the invention will become apparent with an understanding of the following detailed description of the invention or upon employment of the invention in practice.

BRIEF DESCRIPTION OF THE DRAWING

A preferred embodiment of the invention has been chosen for detailed description to enable those having ordinary skill in the art to which the invention appertains to readily understand how to construct and use the invention and is shown in the accompanying drawing in which:

FIG. 3 is a side elevation of a rotary translator.

FIG. 4a is a side elevation view of the rotary drum.

FIG. 4b is a longitudinal section view of the rotary drum of FIG. 4a.

FIG. 5 is a front elevation of anti-backup disc.

FIG. 7 is an exploded view of components of a modified embodiment of anti-backup mechanism according to the invention.

FIG. 8 is a front elevation view of anti-backup spring of the embodiment of FIG. 7.

FIG. 9 is a front elevation view of anti-backup spring of the embodiment of FIG. 7 showing the position of a reciprocal translator.

FIGS. 10a-e are sequential views of the anti-backup mechanism of Figures undergoing full reciprocal motion in relation to the anti-backup spring.

FIGS. 11 and 12 are perspective views of the mechanism of FIG. 7 showing positions of spring and spring blades and reciprocal translator in travel in opposite directions.

DETAILED DESCRIPTION OF THE PREFERRED EMBODIMENT

Figure 1:
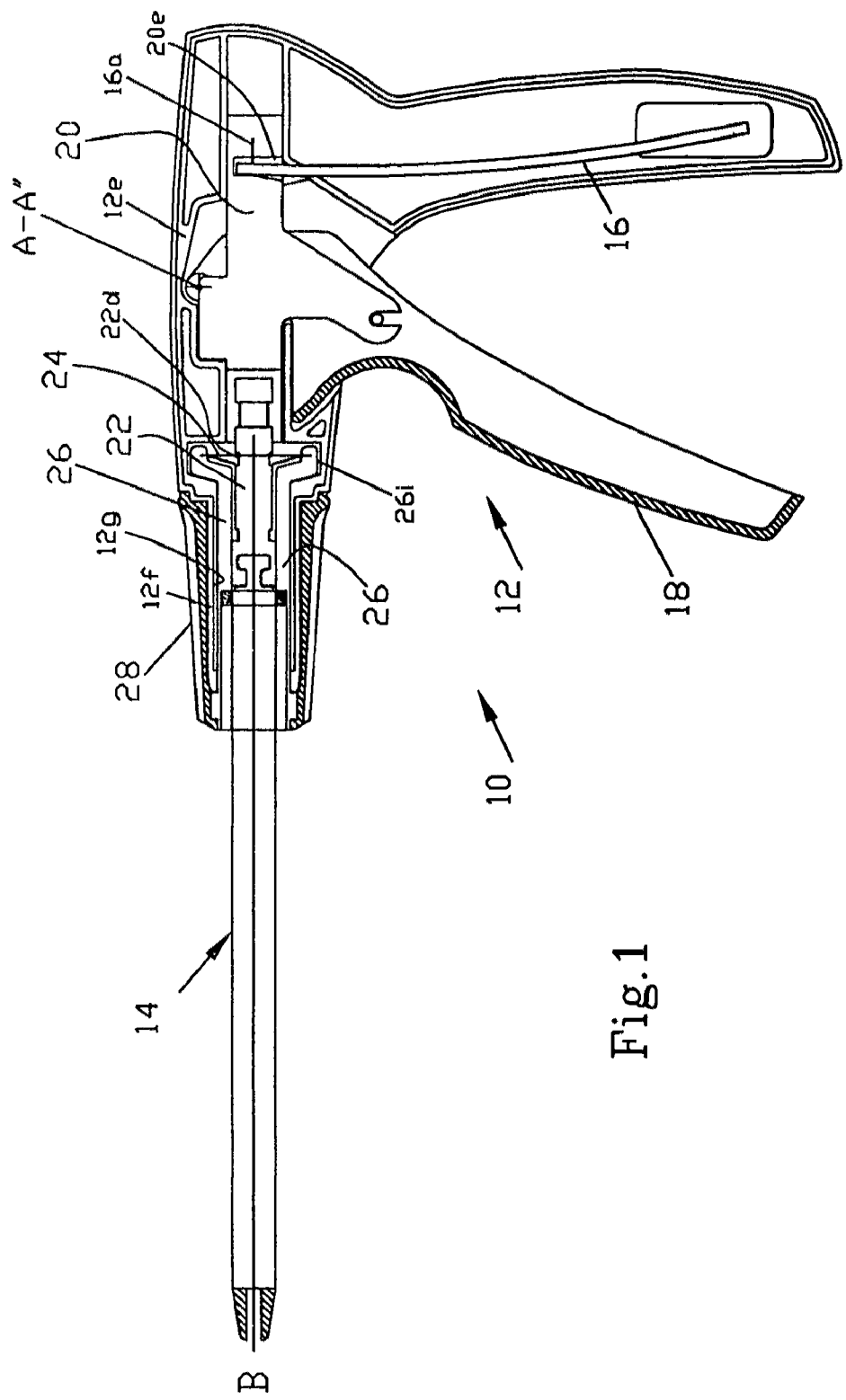
FIG. 1 is a side elevation view of the applicator of FIG. 1 with the operating handle housing partially in section and with handles in release position.

Referring to the drawing, a preferred embodiment of the repeating multi-clip applier 10 comprises operating handle housing 12 and clip applicator cartridge 14.

Figure 2:
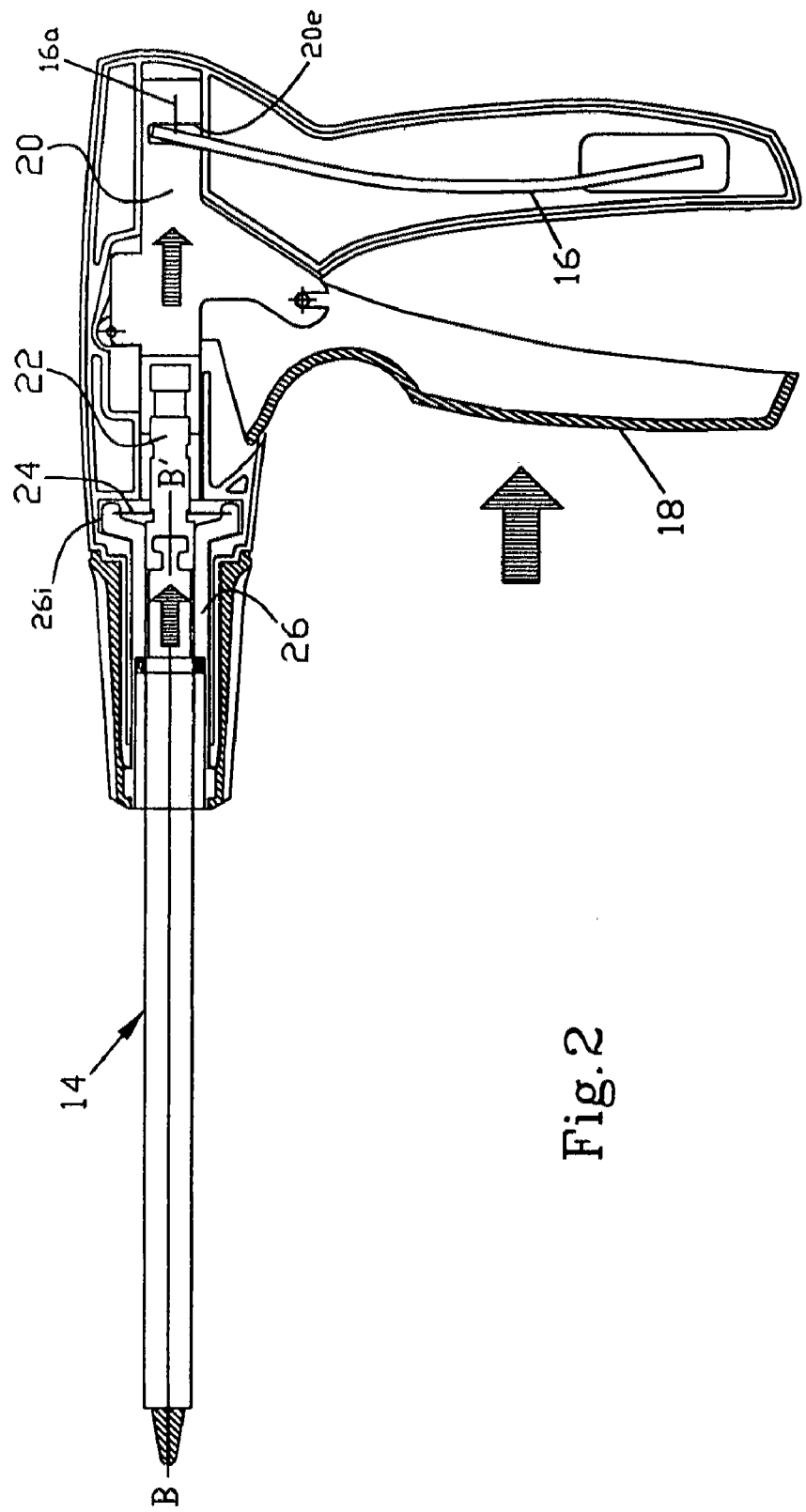
FIG. 2 is a side elevation view of the applicator of FIG. 1 with the operating handle housing partially in section and with handles in pull position.

The operating handle housing 12 shown in FIGS. 1-2 comprises handle members including a depending grip 12c, a center section defining a central chamber 12e, and a forward cylindrical portion 12f defining a forward chamber 12g.

A trigger 18 for actuating applier mechanisms is mounted on the housing for pivotal movement about axis A-A', normal to FIG. 1. The trigger includes a depending grip portion 18.

The trigger when pulled transmits motion to the clip cartridge mechanism (not shown) through the intermediation of fixed translator slide 20 and a rotary translator 22. The trigger acts against the forward bias of bar spring 16 with its end 16a held by translator slide recess 20a.

Figures 3, 4A, 4B, 5:
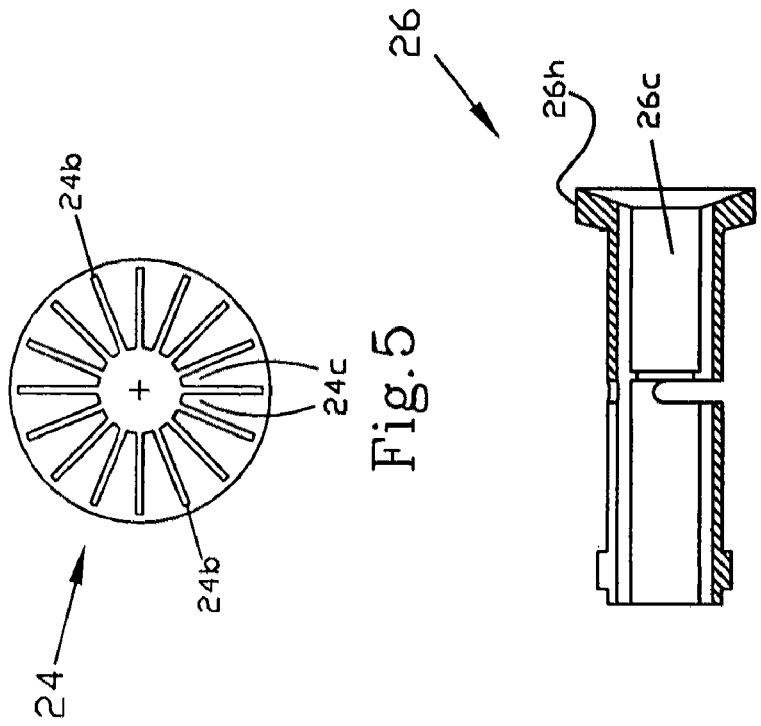

The rotary translator 22 (FIGS. 1, 2, and 3) forms a subassembly with an anti-backup mechanism 24, a rotatable drum 26, and a thumb wheel hub 28 which subassembly interconnects the fixed translator 20 and the clip cartridge 14 for performing the functions of transmitting reciprocating rectilinear motion with a fixed excursion, accommodating rotary motion of the clip cartridge, enabling mounting and disconnecting of the clip cartridge from the operating handle, and providing an anti-backup capability for the operating handle and cartridge mechanism.

The rotary drum subassembly 22, 24, 26 comprises the rotary translator 22 positioned axially within the drum 26. An anti-backup disc 24 (FIGS. 2, 3 and 5), defined by an open center 24a and extending radially from the center to define a plurality of inwardly directed spring fingers 24c, fits onto the rotary translator 22 and is assembled to the enlarged rear end flange 26h of the rotary drum by means of a drum cap 26i (FIGS. 1 and 2). In normal position of the clip applicator with the trigger released, the anti-backup spring fingers 24c are located in the rear anti-backup groove as shown in FIG. 1.

The rotary drum subassembly is assembled into the forward chamber 12g of the operating handle housing. The center section 22c (FIG. 3) of the rotary translator shaft has spaced anti-backup grooves 22d, 22e with the distance between the grooves being approximately equal to the distance of reciprocating rectilinear motion of the fixed translator and equal to the rectilinear excursion of the clip applicator mechanism.

The operation of the anti-backup mechanism is illustrated in FIGS. 6a-g.

Figure 6:
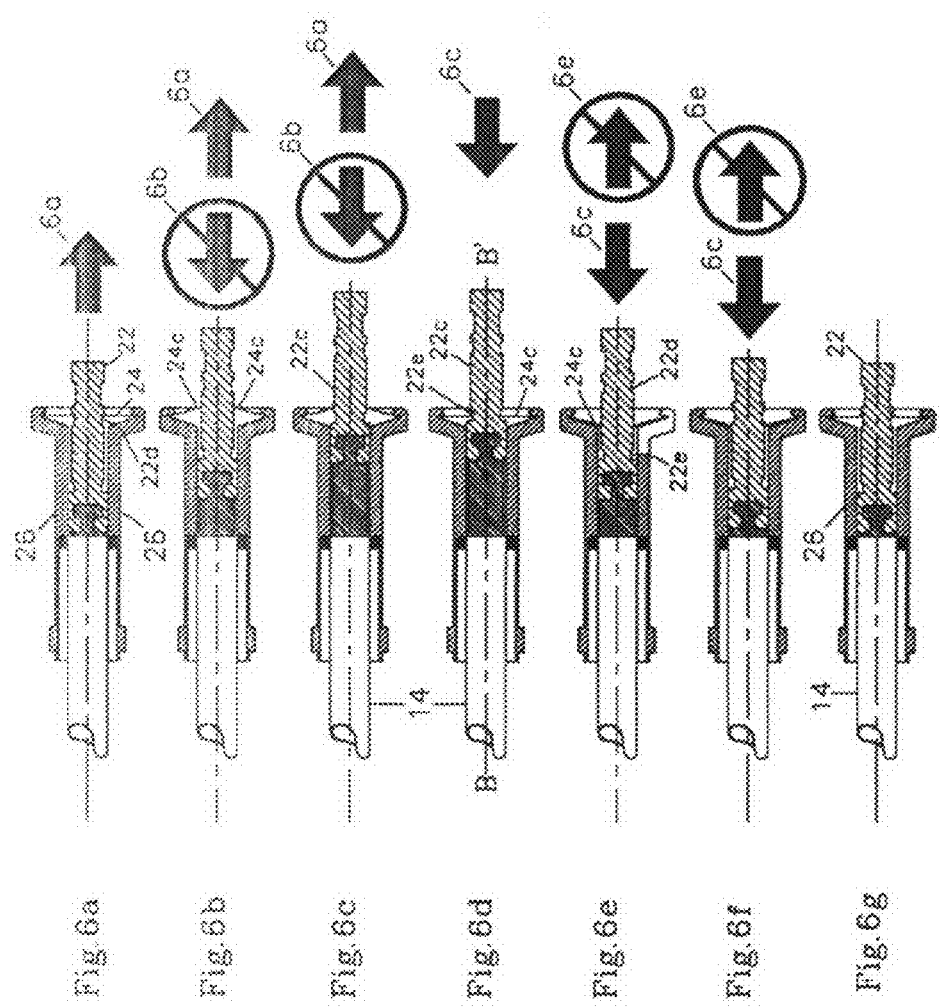
FIGS. 6a-g are sequential views of anti-backup mechanism with disc in (a) rear groove, (b)&(c) between grooves, (d) in front groove, (e)&(f) between grooves, and (g) again in rear groove, and with arrows indicating directions of permitted and prevented movement of operating handle and cartridge mechanism.

In the mechanism position of FIGS. 1 and 6a, the handle trigger 18 is in released position with the anti-backup disc 24 in registry with the rear anti-backup groove 22d of the rotary translator 22. When the trigger is pulled (FIG. 2) (for crimping and applying a clip at a surgical site), the rotary translator moves in the direction of arrow 6a. As the rotary translator continues movement, the spring fingers 24c of the disc engage the outer surface 22c of the rotary translator in the manner shown in FIGS. 6b-c. The anti-backup mechanism applied by the canted spring fingers 24c (FIGS. 6b-c) to the outer surface 22c of the rotary translator permits continued movement in the direction of arrow 6a and prevents movement in the opposite direction of arrow 6b. If a surgeon releases the trigger with less than a full pull stroke leaving anti-backup components in the position of FIG. 6c, for example, the anti-backup mechanism holds the rotary translator in position against the bias of bar spring 16 which tends to return the trigger to release position. In this FIG. 6c hold position, the applicator jaws retain the partially crimped clip preventing it from falling into a surgical site. A continuing pull of the trigger (in direction of arrow 6a) moves the rotary translator through the position of FIG. 6c to the position of FIG. 6d in which the spring fingers 24c enter the forward groove 22

In this position (FIG. 6d), the rotary translator may now be moved forward (by releasing the trigger and by force of return spring 16) in the direction of arrow 6c. In this forward movement, the spring fingers 24c are effective to allow continued forward movement while preventing movement in the direction of arrow 6e. If the handle trigger is held by a surgeon with components as in FIG. 6f, the anti-backup mechanism will prevent the surgeon from pulling the trigger in the direction of arrow 6e. The surgeon must allow full release of the trigger to component position of FIG. 6g. Direction of movement can be changed again when the spring fingers 24c enter the rear groove 22e as in FIG. 6g.

A pull on the trigger against the force of bar spring produces unitary rearward rectilinear movement of the fixed translator, the rotary translator passing through the stationary spring fingers of the anti-backup disc, and the puller bar emerging from within the cartridge casing until the trigger and fixed translator reach the end of travel and with the anti-backup disc spring fingers positioned at the front groove. The rearward excursion is now complete, and when the trigger is released, the bar spring urges the fixed translator forward until all components reach normal position.

In the event a pull on the trigger is released without reaching the full extent of rectilinear motion, the anti-back up spring fingers will not have reached their front groove remaining instead in contact with the outer surface of the rotary translator. The spring fingers in contact with outer surface function as a brake against the action of the bar spring tending to force the released components to return to normal position. In this partial pull condition of the trigger a clip has been crimped in the instrument jaws which clip will fall out of the jaws into a surgical site if the jaws reopen by return of the mechanism to normal position. So the anti-backup mechanism retains the instrument in "partial pull position" against the normalizing force of the bar spring and most importantly prevents fallout from the jaws of a partially crimped clip. The anti-backup device retaining action is removed simply by means of a full pull on the trigger causing the spring fingers to enter the forward groove where they can go "over center" thereafter permitting the rotary translator to pass through the spring fingers. It is to be noted that the anti-backup mechanism is effective in both directions. The anti-backup mechanism has effect when the trigger is released after a full pull so that if there is a "partial release" of the trigger, the trigger must nonetheless return to normal position with full release of the trigger before allowing the trigger to be pulled. The design requirement for full release achieved by the anti-backup mechanism prevents double loading of clips into cartridge jaws.

It is a further aspect of the anti-backup mechanism that the cartridge may be rotated on the B-B' axis as the anti-backup mechanism holds the instrument in partial pull position enabling a surgeon to adjust cartridge or jaw position even after a partial pull has occurred.

A modified embodiment of the invention is shown in FIGS. 7-12 wherein the anti-backup mechanism 30 assembly comprises a reciprocal translator 32, an anti-backup spring 34 and a stationary mounting pocket 36.

The reciprocal translator 32 is an active component of an operating mechanism (not shown) and is assigned a task in the mechanism which is accomplished by back and forth movement or excursion over a fixed distance. Motion is imparted to the reciprocal translator either directly or indirectly by means forming part of the operating mechanism, usually a manually operated component whose action may be stopped in midstroke by its operator. A typical operating mechanism of this sort is a surgical instrument in the hands of a surgeon performing a medical procedure.

The translator has a block body with rectangular cross-section and generally planar parallel opposite sides 32a-b, and 32c-d (FIGS. 11-12). Opposite sides (e.g., 32c and 32d) have transition points 32e defined by first and second sets of recesses 32f in their surfaces. A recess may be aligned grooves 32h (one set) or shoulders 32i (another set) on opposites sides of the translator. The transition points on the translator are spaced apart a distance equal to the excursion assigned to the translator as a component of the operating mechanism. As will be fully understood with description of the anti-backup spring next below, the transition points allow for spring action on the translator to be neutralized as the spring registers with the transition points.

The anti-backup spring 34 preferably comprises a rectangular sheet of spring steel with, its interior portion removed as by metal stamping to define an interior opening 34f leaving a unitary body with side struts 34a-b and end struts 34c-d. Spring blades 34e integral with the end struts project inwardly of the spring interior opening 34f with spring blade edges 34g in generally parallel, confronting relation. As shown in FIG. 9, the spring interior 34f accommodates a cross-section of the body of the reciprocal translator for both reciprocal movement as well reversal of movement. In FIG. 9 the spring blades are shown in position at translator transition points 32e. The spring may be fabricated of any suitable material that can be formed into the spring shape shown in FIGS. 8, 11 and 12 and perform the spring action required of blades 34e.

The translator and spring are assembled with a support housing preferably in the form of stationary mounting pocket 36 situated within a host operating mechanism. The mounting pocket is a U-shape housing 36a defining a pocket or chamber 36b between confronting arms 36c for receiving the reciprocal translator body. Each arm has a recess in the form of a V-shape channel 36d with opposed channels being aligned for receiving and holding anti-backup spring 34 by their side struts 34a-b as shown in FIG. 10. Referring to FIG. 7, the mechanism is assembled by inserting spring 34 into channels 36d and by passing the translator through the spring interior 34f until spring blades 34e register with transition grooves 32h.

FIGS. 10a-e illustrate operation of the anti-backup spring mechanism from:
  stop (FIG. 10) with spring blades 34e in registry with transition shoulder 32i;
  motion to the right (FIGS. 10b and 12) where blade edges 34e engage the sides 32c-d of the translator and deflect in the direction of motion allowing the translator to continue moving right and preventing by digging-in engagement with sides 32c-d any reverse movement of the translator;
  registry (FIG. 10c) of spring blade edges 34e with transition groove 32h where the restraining effect of the blade edges is neutralized and rightward movement of the translator stops;
  reversal of movement (FIGS. 10d and 11) where the spring blades now bow in the direction of travel of the translator; and stop (FIG. 10e) where the blades again register with transition shoulders 32i Various changes may be made to the structure embodying the principles of the invention. The foregoing embodiments are set forth in an illustrative and not in a limiting, sense. The scope of the invention is defined by the claims appended hereto.

I claim:

1. An anti-backup mechanism for a device having linear reciprocating motion through forward and reverse strokes over a distance defining a fixed excursion, the anti-backup mechanism comprising a reciprocal translator having a body with opposite generally parallel sides, the opposite sides having first and second spaced transition points formed into the sides at a distance substantially equal to the fixed excursion, an anti-backup sheet spring having its interior portion removed to define an interior opening leaving a unitary body with side struts and end struts, spring blades integral with the end struts projecting within the spring interior opening, with spring blade side edges spaced from the side struts, and with spring blade inner edges in generally parallel, confronting relation for engaging the opposite generally parallel sides of the reciprocal translator wherein the spring interior opening accommodates a cross-section of the body of the reciprocal translator for both forward and reverse strokes over a fixed excursion, a support housing having aligned recesses for receiving and holding the spring in operative position to receive the reciprocal translator in the interior opening whereby movement of the translator is confined to full fixed excursion between first and second transition points.

2. An anti-backup mechanism for a device having linear reciprocating motion through forward and reverse strokes over a distance defining a fixed excursion, the anti-backup mechanism comprising a reciprocal translator having a body with opposite generally parallel sides, the opposite sides having first and second spaced transition points formed into the sides at a distance substantially equal to the fixed excursion, an anti-backup sheet spring having its interior portion removed to define an interior opening leaving a unitary body with side struts and end struts, spring blades integral with the end struts projecting within the spring interior opening, with spring blade side edges spaced from the side struts, and with spring blade inner edges in generally parallel, confronting relation for engaging the opposite generally parallel sides of the reciprocal translator wherein the spring interior opening accommodates a cross-section of the body of the reciprocal translator for both forward and reverse strokes over a fixed excursion, a U-shape support housing defining a pocket for accommodating the translator in reciprocal motion through said fixed excursion, the support housing having aligned recesses for receiving and holding the spring in operative position to receive the reciprocal translator in the interior opening of the spring whereby movement of the translator is confined to full fixed excursion between first and second transition points.

3. An anti-backup mechanism as defined in claim 2 in which first and second spaced transition points are recesses in the sides of the translator.

4. An anti-backup mechanism as defined in claim 3 in which a first one of the recesses is a shoulder, and the other recess is a channel formed by adjacent shoulders.

5. An anti-backup mechanism as defined in claim 3 in which the shoulder recess is at an end of the translator first inserted into the pocket.

6. An anti-backup mechanism as defined in claim 3 in which the support housing has V-shape recesses aligned on opposite sides of the pocket for receiving and holding the spring in operative position.

\* \* \* \* \*